US011512043B2

(12) United States Patent
Treskow et al.

(10) Patent No.: US 11,512,043 B2
(45) Date of Patent: Nov. 29, 2022

(54) PROCESS FOR PREPARING N-METHYL(METH)ACRYLAMIDE

(71) Applicant: EVONIK OPERATIONS GMBH, Essen (DE)

(72) Inventors: Marcel Treskow, Darmstadt (DE); Doris Saal, Bensheim (DE); Thorben Schütz, Alsbach-Hähnlein (DE); Steffen Krill, Mühltal (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/262,735

(22) PCT Filed: Jul. 16, 2019

(86) PCT No.: PCT/EP2019/069082
§ 371 (c)(1),
(2) Date: Jan. 24, 2021

(87) PCT Pub. No.: WO2020/020698
PCT Pub. Date: Jan. 30, 2020

(65) Prior Publication Data
US 2022/0112154 A1  Apr. 14, 2022

(30) Foreign Application Priority Data

Jul. 26, 2018  (EP) .................... 18185792

(51) Int. Cl.
*C07C 231/02* (2006.01)
*C07C 231/24* (2006.01)
*C08F 220/56* (2006.01)

(52) U.S. Cl.
CPC .......... *C07C 231/02* (2013.01); *C07C 231/24* (2013.01); *C08F 220/56* (2013.01)

(58) Field of Classification Search
None
See application file for complete search history.

(56) References Cited

U.S. PATENT DOCUMENTS

| | | | |
|---|---|---|---|
| 3,642,877 A | 2/1972 | Jayawant | |
| 3,850,988 A | 11/1974 | Ruby | |
| 4,215,195 A | 7/1980 | Ponticello et al. | |
| 4,672,105 A | 6/1987 | Schlosser et al. | |
| 4,745,213 A | 5/1988 | Schlosser et al. | |
| 5,395,892 A | 3/1995 | Haeberle et al. | |
| 6,008,404 A | 12/1999 | Miller et al. | |
| 6,706,910 B2 | 3/2004 | Iwakura et al. | |
| 8,420,709 B2 | 4/2013 | Breiner et al. | |
| 8,669,328 B2 | 3/2014 | Breiner et al. | |
| 8,742,163 B2 | 6/2014 | Knebel et al. | |
| 9,512,062 B2 | 12/2016 | Knebel et al. | |
| 9,656,941 B2 | 5/2017 | Kleese et al. | |
| 10,343,980 B2 | 7/2019 | Krill et al. | |
| 10,407,701 B2 | 9/2019 | Kim et al. | |
| 2006/0142408 A1 | 6/2006 | Liu et al. | |
| 2011/0196169 A1 | 8/2011 | Knebel et al. | |
| 2011/0218312 A1 | 9/2011 | Knebel et al. | |
| 2014/0288330 A1 | 9/2014 | Broell et al. | |
| 2016/0297738 A1 | 10/2016 | Klesse et al. | |
| 2019/0352251 A1 | 11/2019 | Hartmann et al. | |
| 2020/0331845 A1 | 10/2020 | Treskow et al. | |
| 2021/0163439 A1 | 6/2021 | Treskow et al. | |
| 2021/0179529 A1 | 6/2021 | Treskow et al. | |
| 2021/0179531 A1 | 6/2021 | Treskow et al. | |
| 2021/0214297 A1 | 7/2021 | Bleith et al. | |
| 2021/0269393 A1 | 9/2021 | Treskow et al. | |
| 2021/0332005 A1 | 10/2021 | Treskow et al. | |

FOREIGN PATENT DOCUMENTS

| | | |
|---|---|---|
| CA | 1340884 | 1/2000 |
| EA | 201501099 | 7/2016 |
| EP | 0016518 | 10/1980 |
| EP | 2246403 | 11/2010 |
| GB | 1193412 | 6/1970 |
| GB | 2162 516 | 2/1986 |
| GB | 2248234 | 4/1992 |
| JP | 2003261506 | 9/2003 |
| SU | 234254 | 1/1969 |
| TW | 201807491 | 3/2018 |
| WO | WO 2009/146995 | 12/2009 |
| WO | WO 2010/021956 | 2/2010 |
| WO | WO 2012/084737 | 6/2012 |
| WO | WO 2017/145022 | 8/2017 |
| WO | WO 2017/147040 | 8/2017 |

OTHER PUBLICATIONS

Airgas: Methylamines (downloaded from https://web.archive.org/web/20160302072912/http://airgasspecialtyproducts.com/products/methylamines/ on Mar. 8, 2022, originally captured by the Wayback Machine on Mar. 2, 2016) (Year: 2016).*
International Search Report for corresponding international application PCT/EP2019/069082, filed Jul. 16, 2019.
Written Opinion of the International Searching Autjority for corresponding international application PCT/EP2019/069082, filed Jul. 16, 2019.
International Preliminary Report on Patentability for corresponding international application PCT/EP2019/069082, filed Jul. 16, 2019.
European Search Report Search Opinion for corresponding European application EP 18 18 5792 filed Jul. 26, 2018 with English language machine translation of the Search Opinion attached.
Casas, et al., "Kinetics of chemical interesterification of sunflower oil with methyl acetate for biodiesel and triacetin production," *Chemical Engineering Journal* 171:1324-1332 (2011).

(Continued)

*Primary Examiner* — Amy C Bonaparte
(74) *Attorney, Agent, or Firm* — Law Office of Michael A. Sanzo, LLC

(57) ABSTRACT

The invention relates to a process for preparing N-methyl (meth)acrylamide and to the uses thereof.

20 Claims, No Drawings

(56) References Cited

OTHER PUBLICATIONS

O'Donnell, et al., "Microstructure, Kinetics, and Transport in Oil-in-Water Microemulsion Polymerizations," *Macromolecular Rapid Communications* 28(14):1445-1454 (2007).
U.S. Appl. No. 16/753,287, filed Apr. 2, 2020, US-2020/0331845 A1, Oct. 22, 2020, Treskow.
U.S. Appl. No. 16/479,497, filed Jul. 9, 2019, US-2019/0352251 A1, Nov. 21, 2019, Hartmann.
U.S. Appl. No. 16/973,995, filed Dec. 10, 2020, Treskow.
U.S. Appl. No. 17/057,659, filed Nov. 21, 2020, Bleith.
U.S. Appl. No. 17/260,223, filed Jan. 14, 2021, Treskow.
U.S. Appl. No. 17/260,226, filed Jan. 14, 2021, Treskow.
U.S. Appl. No. 17/268,463, filed Feb. 13, 2021, Treskow.
U.S. Appl. No. 17/268,465, filed Feb. 13, 2021, Treskow.

\* cited by examiner

PROCESS FOR PREPARING N-METHYL(METH)ACRYLAMIDE

CROSS REFERENCE TO RELATED APPLICATIONS

The present application is US national stage of international application PCT/EP2019/069082, which had an international filing date of Jul. 16, 2019 and which was published on Jan. 30, 2020. The application claims priority to EP 18185792.1, filed on Jul. 26, 2018. The contents of the priority application is hereby incorporated by reference in its entirety.

The invention relates to a process for preparing N-methyl (meth)acrylamide.

N-Methyl(meth)acrylamide can be prepared by reaction with acid halide and methylamine. In this case, however, an additional equivalent of base is required, by which the hydrogen halide formed is scavenged. In the case of doubt, this is methylamine itself, which would require two equivalents of methylamine, which would adversely affect the economic viability of the preparation.

A further preparation is described in general terms by DE4027843, a continuous process for preparing N-substituted acrylamides and methacrylamides. In this process, by reaction of alkyl esters of acrylic acid or methacrylic acid with aliphatic or aromatic amines in a molar ratio of 2 in continuous mode, the corresponding N-substituted acrylamides and methacrylamides are obtained. Like the preparation with acid chlorides, this process requires two equivalents of the amine and is therefore only of limited atom economy. Although the reaction does not need a catalyst, it proceeds under severe conditions at >150° C. and a pressure of about 160 bar. If N-methylmethacrylamide is prepared with more amine than the stoichiometric amount of methacrylic anhydride, a vacuum-unstable salt is formed. In the subsequent workup, it breaks down, and so the vacuum cannot be maintained, the temperature rises in an uncontrolled manner and the product ultimately polymerizes.

DE102011089363 likewise discloses the preparation of N-alkyl(alkyl)acrylamides, likewise proceeding from the corresponding acid anhydride and alkylamine. What is claimed here is the addition of the amine in aqueous solution, and neutralization of the solution prior to removal of the product. For the preparation of N-methyl(meth)acrylamide, preparation in aqueous solution is very unfavourable. N-Methyl(meth)acrylamide is a liquid, dissolves in water in any ratios, can only be extracted with great difficulty and results in very high losses owing to similar boiling points on distillative separation. However, the use of aqueous solutions of the amine has the crucial advantage that the ammonium salt of the acid formed as an intermediate is forced into a dissociation equilibrium in the presence of water. As a result, there are always small traces of amine in the system, which can react with the anhydride, such that the overall yield reaches >95%.

WO 2010/021956 discloses the preparation of N-alkyl (alkyl)acrylamides, likewise proceeding from the corresponding acid anhydride and alkylamine. What is claimed here is the addition of the anhydride to the amine in the form of an initially charged aqueous solution. This process variant is associated with significant exothermicity, which can cause discolouration. Furthermore, the same disadvantages exist as in DE102011089363.

The problem addressed was that of providing a particularly economically reliable process for preparing N-methyl (meth)acrylamide.

The problem was solved by a process for preparing N-methyl(meth)acrylamide by reacting (meth)acrylic anhydride and methylamine in the absence of water.

More particularly, the problem was solved by a process for preparing N-methyl(meth)acrylamide,
characterized in that
a) (meth)acrylic anhydride is reacted with methylamine,
b) the methylamine has a water content of <10% by weight,
c) the stoichiometry of anhydride:amine is less than 1:2.

It has been found that, surprisingly, the process according to the invention achieves virtually quantitative yields, and the losses on workup to give a pure material are particularly low. Moreover, the (meth)acrylic acid by-product can be reused as starting material for the preparation of the anhydride, and so the reaction has complete atom economy and is thus not just particularly efficient but also very sustainable.

It has been found that the process according to the invention can be conducted particularly advantageously when the reaction is virtually anhydrous.

Furthermore, it has been found that the reaction can be conducted without addition of catalyst, which leads to a further improvement in the economic viability of the process.

The notation "(meth)acrylate" here means both methacrylate, for example methyl methacrylate, ethyl methacrylate, etc., and acrylate, for example methyl acrylate, ethyl acrylate, etc., and mixtures of the two.

Catalyst

The reaction can be conducted in the absence of catalysts. The reaction is sufficiently rapid without addition of catalyst.

(Meth)Acrylic Anhydride (Meth)acrylic anhydride used is methacrylic anhydride or acrylic anhydride.

Stabilizer

The (meth)acrylic anhydride is preferably used in stabilized form. Suitable stabilizers are: phenothiazine, 2,4-dimethyl-6-tert-butylphenol, N,N'-diphenyl-p-phenylenediamine, 4-hydroxy-2,2,6,6-tetramethylpiperidinooxyl, 4-methyl-2,6-di-tert-butylphenol, 2-tert-butyl-6-(3-tert-butyl-2-hydroxy-5-methylbenzyl)-4-methylphenyl acrylate, benzene-1,4-diamine, N,N'-mixed phenyl and tolyl derivatives (DTPD), 2,6-di-tert-butyl-alpha-(dimethylamino)-p-cresol, tert-butylcatechol, bis-2,2,6,6-tetramethyl-4-piperidyl sebacate, 2,2,6,6-tetramethylpiperidine N-oxyl and mixtures thereof.

The amount of stabilizer is introduced into the reactor with (meth)acrylic anhydride as a solution at the start of the reaction, initially charged or added after the (meth)acrylic anhydride.

Methylamine

Methylamine can be used in liquid form, in gaseous form (for example monomethylamine, from GHC Gerling, Holz+ Co, Hanau, Germany) or in anhydrous solvents, for example in THF, MTBE, acetonitrile, chloroform, dichloromethane or diethyl ether. Aqueous methylamine solutions are unsuitable for this process.

Preferably, the water content of the methylamine is <10% by weight, preferably <5% by weight, more preferably <1% by weight and most preferably <0.1% by weight.

Preferably, the water content of the reaction mixture after the end of addition of all reactants is <10% by weight, preferably <5% by weight, more preferably <1% by weight and most preferably <0.1% by weight.

Solvent

The reaction can be effected without solvent, or in the presence of solvents. Suitable solvents are selected from the group of: THF, MTBE, diethyl ether, dioxane, acetonitrile, nitromethane, chloroform, dichloromethane, benzene or toluene and mixtures thereof.

Reaction Conditions

The reaction is effected at temperatures between −20° C. and 100° C., preferably between 0° C. and 80° C. and more preferably between 20° C. and 50° C.

To avoid the formation of unwanted by-products, a particularly low temperature is employed in order to prevent the Michael addition of amines onto the double bond of the (meth)acrylate.

The (meth)acrylic anhydride is reacted with methylamine at an absolute pressure of 0.5 bar to 10 bar, preferably 1 bar to 5 bar.

The reaction time is in the range of 0.1-10 h, preferably 0.5-5 h.

Stoichiometry

The stoichiometry of (meth)acrylic anhydride:amine is less than 1:2, preferably less than 1:1.5, more preferably less than 1:1.1 and most preferably exactly 1:1.

In a further process version in which ambient pressure is employed, it is also possible to bubble methylamine into the reaction solution. In this case, not all the methylamine reacts. What is crucial to the success of the reaction is that the excess of the amine reacted to (meth)acrylic anhydride is between 0.5 and 1.5.

Neutralization and Workup:

The crude product obtained can be worked up directly after the end of the reaction by means of a fractional distillation without any need for neutralization.

Preferred Method Variants

The (meth)acrylic anhydride is initially charged in an autoclave and the autoclave is screwed shut. The steel methylamine gas bottle is connected to the autoclave by a coiled VA feed pipe, and the decrease in weight on introduction of methylamine is monitored.

The introduction of methylamine is commenced with a feed rate of about 4 g/3 min at room temperature. The reaction is strongly exothermic. The temperature should not exceed 40° C. (35° C.±5° C.). The mixture is cooled with an acetone-dry ice mixture. The metering rate is increased to 6 g/3 min of methylamine. Once the stoichiometric amount of methylamine has been introduced, the bottle is closed, the remaining gas in the conduit is left to react for 10 min and then the cooling is removed and the autoclave is vented.

An alternative method is reaction in the presence of solvents. (Meth)acrylic anhydride and a suitable solvent, for example MTBE, are initially charged and cooled. The methylamine gas is introduced at about 2° C.-10° C. The reaction is weakly exothermic.

Since the reaction proceeds only very gradually at this temperature, gas may be introduced at a faster rate. The bottom temperature can rise to up to 50° C. The introduction is ended when no (meth)acrylic anhydride is detectable any longer. The solvent is drawn off, for example with a rotary evaporator. The residue is distilled.

The N-methyl(meth)acrylamides prepared in accordance with the invention find use as copolymer in (meth)acrylate polymers in order to increase the water solubility of a polymer.

The examples given hereinafter are given for better illustration of the present invention, but are not capable of restricting the invention to the features disclosed therein.

The methacrylic anhydride used in the present examples has always been stabilized with 2000 ppm of 2,4-dimethyl-6-tert-butylphenol.

EXAMPLE 1: PREPARATION OF N-METHYLMETHACRYLAMIDE

Reaction Equation:

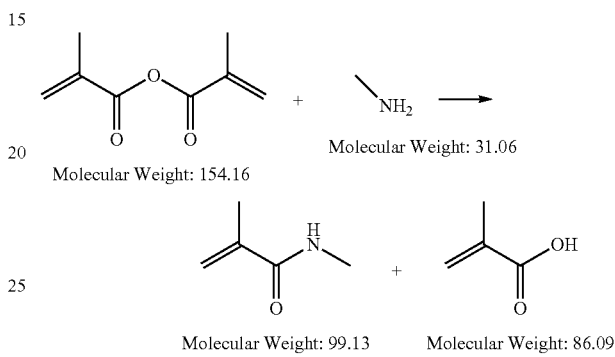

Molecular Weight: 154.16

Molecular Weight: 31.06

Molecular Weight: 99.13

Molecular Weight: 86.09

Apparatus: 2 L autoclave with glass insert, Ni—Cr—Ni thermocouple, gas feed: metal, steel methylamine gas bottle, manometer, acetone/dry ice bath Mixture:

| | | |
|---|---|---|
| 6.0 mol | methacrylic anhydride = | 940.2 g |
| 6.0 mol | methylamine, gas = | 186.4 g |

Theoretical Yield:

(=starting weight) 1126.6 g

Procedure:

The methacrylic anhydride is initially charged in the glass insert of the autoclave and the autoclave is screwed shut. The steel methylamine gas bottle is on a balance and is connected to the autoclave by a coiled VA feed pipe; hence the decrease in weight on introduction of methylamine can be monitored.

The introduction of methylamine is commenced with a metering rate of about 4 g/3 min at room temperature. The reaction is strongly exothermic. The temperature should not exceed 40° C. (35° C.±5° C.). The mixture is cooled with an acetone-dry ice mixture. The metering rate is increased to 6 g/3 min of methylamine; no more is possible due to the cooling as a result of the poor heat transfer owing to the glass insert. Once the stoichiometric amount of methylamine (186.4 g, 6 mol) has been introduced, the bottle is closed, the remaining gas in the conduit is left to react for 10 min and then the cooling is removed and the autoclave is vented.

Yield: 1125 g

GC of the product, method: (GC: DB5, 30 m, Ø 0.25 mm, film thickness 0.25 μm, 50° C., 3 min isothermal, 14° C./min→280° C., 8 min isothermal; det: 280° C., inj.: 250° C.)

| Name Retention: | Methyl-amine 1.08 min | Methacrylic acid 3.83 min | N-Methyl-methacrylamide 5.97 min | Methacrylic anhydride 7.43 min | HB 13.15 min |
|---|---|---|---|---|---|
| GC area % | 0.045 | 41.360 | 52.445 | 0.079 | 4.187 |

HB = high boilers

EXAMPLE 2: WORKUP OF N-METHYLMETHACRYLAMIDE BY DISTILLATION

Apparatus: 2 l three-neck round-bottom flask with boiling capillary, Pt100 temperature sensor, 30 cm mirrored column with 8×8 Raschig rings, automatic column head (liquid divider), reflux condenser, coiled condenser, Thiele-Anschutz attachment, receivers, oil bath, vacuum pump, manometer Mixture:

| | | |
|---|---|---|
| 1122 g | N-methylmethacrylamide from Example 1 | |
| 22.4 mg | 4-hydroxy-2,2,6,6-tetramethylpiperidinooxyl (rad.) | (20 ppm) |
| 224.4 mg | hydroquinone monomethyl ether | (200 ppm) |
| 1122 mg | octadecyl 3-(3,5-di-tert-butyl-4-hydroxyphenyl)propionate | (1000 ppm) |

Procedure:

| Bath °C. | Bottom °C. | Top °C. | Pressure mbar | Comment |
|---|---|---|---|---|
| 28 | 28 | 28 | 13.0 | start of heating |
| 108 | 88.9 | 50 | 4.0 | boils, RR 1:5; 1st fraction |
| 111 | 99.2 | 58 | 3.8 | 2nd fraction |
| 112 | 100.4 | 62 | 3.8 | 3rd fraction |
| 128 | 114.7 | 69 | 2.9 | 4th fraction |
| 134 | 119.6 | 89 | 2.8 | 5th fraction |
| 136 | 113 | 91 | 2.9 | RR 1:10 |
| 141 | 118 | 91 | 2.8 | RR 1:5 |
| 146 | 122 | 94 | 2.8 | 6th fraction |
| 147 | 122.6 | 94 | 2.7 | 7th fraction |
| 131 | 104 | 77 | 2.4 | 8th fraction |
| 138 | 105.9 | 79 | 2.3 | 9th fraction |
| 139 | 106.4 | 79 | 2.3 | 10th fraction |
| 144 | 108.5 | 79 | 2.3 | RR 1:2.5 |
| 144 | 108.0 | 80 | 2.3 | RR 1:1 |
| 143 | 110.4 | 81 | 2.3 | 11th fraction |
| 153 | 130 | 77 | 2.3 | end |

RR = reflux ratio

Yield and GC Analyses:

| Name Retention: [min] Fraction | Amount g | Methyl-amine 1.08 min | Methacrylic acid 3.83 min | N-Methyl-methacrylamide 5.97 min | Methacrylic anhydride 7.43 min | HB 2 8.71 | HB 3 10.89 | HB 1 13.15 |
|---|---|---|---|---|---|---|---|---|
| 1st | 135.7 | 0.003 | 99.867 | 0.124 | | | | |
| 2nd | 139.1 | 0.007 | 99.993 | | | | | |
| 3rd | 84.2 | 0.004 | 99.938 | 0.037 | | | | |
| 4th | 50.4 | | 97.275 | 1.758 | 0.008 | 0.77 | | |
| 5th | 58.0 | 0.018 | 62.601 | 33.538 | 0.007 | 3.44 | | |
| 6th | 28.8 | | 38.609 | 56.422 | 0.008 | 4.52 | | |
| 7th | 30.4 | | 22.935 | 72.339 | 0.005 | 4.30 | | |
| 8th | 73.3 | | 7.300 | 90.296 | | 2.12 | | |
| 9th | 38.5 | | 3.850 | 94.531 | | 1.15 | 0.011 | |
| 10th | 230.3 | | 0.929 | 98.566 | | 0.36 | 0.060 | 0.011 |
| 11th | 113.6 | | 0.116 | 99.120 | | 0.23 | 0.339 | 0.053 |
| Cold trap 1 | 8.5 | 0.004 | | 99.921 | 0.067 | | | |
| Cold trap 2 | 1.5 | 0.027 | 65.237 | 30.016 | 3.97 | | | |
| Residue * | 75.6 | | 1.285 | 14.950 | | 3.100 | 20.60 | |

* viscous, further peaks: 11.257 min: 25.653%; 11.688 min: 15.458%; 12.259 min: 5.177% + further smaller peaks

EXAMPLE 3: PREPARATION OF N-METHYLMETHACRYLAMIDE IN SOLVENT

Apparatus:

1 l four-neck round-bottom flask with precision glass stirrer (Teflon sleeve), Pt100 temperature sensor, gas inlet (Teflon), gas outlet of Teflon with wash bottles as safety bottles, reflux condenser, steel methylamine gas bottle, waste air conduit directly into the fume hood, feed for compressed air as added air, acetone/dry ice cooling bath Mixture:

| 1.0 mol | methacrylic anhydride = 156.4 g |
| 250 ml | methyl tert-butyl ether (MTBE) |
| 1.0 mol | methylamine, gas |

Theoretical Yield:

99.1 g

Procedure:

Methacrylic anhydride and MTBE are initially charged and cooled. The methylamine gas is introduced at about 2° C.-10° C. The reaction is weakly exothermic.

Since the reaction proceeds only very slowly at this temperature, gas is introduced more quickly and the bottom temperature can be increased to up to 50° C. The introduction is ended when no methacrylic anhydride is detectable any longer. The MTBE is drawn off on a rotary evaporator (RE) at a bath temperature of 60° C. and a pressure down to 200 mbar.

Distillate to 200 mbar: 151.5 g

Residue to 200 mbar: 181.7 g

The residue (180 g) is distilled through a 15 cm Vigreux column under reduced pressure with addition of 1000 ppm of octadecyl 3-(3,5-di-tert-butyl-4-hydroxyphenyl)propionate, 500 ppm of hydroquinone monomethyl ether and 20 ppm of 4-hydroxy-2,2,6,6-tetramethylpiperidinooxyl (rad.).

| Bath [° C.] | Bottom [° C.] | Top [° C.] | Pressure mbar | Comment | Mass |
|---|---|---|---|---|---|
| 24 | 24 | 24 | 3.8 | start of heating | |
| 83 | 64.7 | 53 | 2.1 | 1st fraction | 62.9 g |
| 85 | 70.5 | 64 | 1.8 | 2nd fraction | 35.3 g |
| 90 | 72.3 | 69.0 | 1.7 | 3rd fraction | 45.0 g |
| 92 | 75.2 | 71 | 1.6 | 4th fraction | 19.7 g |
| 103 | 84.3 | 70 | 1.6 | Thermometer no longer immersed | |
| 111 | 96.9 | 50 | 1.6 | end | 13.5 g |

Analyses:

(GC: DB5, 30 m, Ø 0.25 mm, film thickness 0.25 μm, 50° C., 3 min isothermal, 14° C./min→280° C., 8 min isothermal; det: 280° C., inj.: 250° C.)

| Name Ret. [min] Probe: | MTBE 1.33 | Methylamine 1.08 | Methacrylic acid 3.83 | N-Methylmethacrylamide 5.97 min | Methacrylic anhydride 7.43 min | HB 1 13.15 |
|---|---|---|---|---|---|---|
| Rct: 1.5 h | * | | 3.38 | 2.96 | 89.70 | 2.18 |
| Rct: 3 h | * | | 14.82 | 16.23 | 59.33 | 4.19 |
| Rct: 5 h | * | | 37.09 | 45.68 | 9.53 | 3.59 |
| Rct: 5.5 h | * | | 40.80 | 51.43 | 0.05 | 3.05 |
| RE distillate | 98.63 | | 1.27 | 0.11 | | |
| RE residue | | 0.06 | 39.95 | 53.65 | 0.01 | 3.87 |
| Dist. 1st fr. | 0.02 | 0.02 | 85.52 | 14.26 | 0.01 | 0.02 |
| Dist. 2nd fr. | | 0.04 | 37.91 | 61.80 | | 0.10 |
| Dist. 3rd fr. | 0.03 | 0.05 | 10.45 | 88.92 | | 0.29 |
| Dist. 4th fr. | | 0.05 | 1.67 | 96.71 | | 0.93 |

* not included in integration

Yield Via GC Analyses:

89.9 g of N-methylmethacrylamide=90.7% of theory

COMPARATIVE EXAMPLE 1: PREPARATION OF N-METHYLMETHACRYLAMIDE IN EXCESS METHYLAMINE GAS

Apparatus:

1 l four-neck round-bottom flask with precision glass stirrer (Teflon sleeve), Pt100 temperature sensor, gas feed of Teflon with wash bottles as safety bottles, gas inlet (Teflon), reflux condenser, steel methylamine gas bottle, waste air conduit directly into the fume hood, feed for compressed air as added air, acetone/dry ice cooling bath Mixture:

1.0 mol methacrylic anhydride=156.4 g 250 ml methyl tert-butyl ether

~2 mol methylamine, gas

Theoretical N-methylmethacrylamide yield: 99.1 g

Procedure:

Methacrylic anhydride and MTBE are initially charged, and methylamine gas is introduced with vigorous stirring. The conversion is monitored by GC. If no methacrylic anhydride is detectable any longer, methylamine is nevertheless introduced further, since an exothermic reaction is still taking place. As soon as this becomes weaker, the introduction is ended. After the stirring has been stopped, 2 phases form. The MTBE is drawn off on a rotary evaporator at bath temperature 60° C. and a pressure down to 200 mbar.

Distillate to 200 mbar: 177.1 g

Residue to 200 mbar: 215.0 g

|  | MTBE 1.328 min | Methyl- amine 1.08 min | Methacrylic acid 3.83 min | N-Methylmeth- acrylamide 5.97 min | Methacrylic anhydride 7.43 min |
|---|---|---|---|---|---|
| 1 h 5 min | * |  | 10.35 | 11.15 | 73.14 |
| 2 h 15 min | * |  | 20.19 | 23.34 | 49.91 |
| 3 h 15 min | * |  | 27.59 | 32.88 | 32.24 |
| 4 h 15 min | * | 1.70 | 40.17 | 51.52 | — |
| 5 h 15 min | * | 5.98 | 37.83 | 46.93 | — |
| Lower phase | * | 8.67 | 35.92 | 45.36 |  |
| Upper phase | * | 10.55 | 11.36 | 68.47 |  |
| Distillate to 200 mbar | 98.01 | 1.99 |  |  |  |
| Residue to 200 mbar |  | 7.36 | 36.33 | 46.47 |  |
| Distillation of 1st fraction |  | 2.42 | 34.07 | 63.32 |  |

* not included 180 g of the rotary evaporator residue is distilled through a 15 cm Vigreux column under reduced pressure with addition of 1000 ppm of octadecyl 3-(3,5-di-tert-butyl-4-hydroxyphenyl)propionate, 500 ppm of hydroquinone monomethyl ether and 20 ppm of 4-hydroxy-2,2,6,6-tetramethylpiperidinooxyl (rad.).

Owing to the breakdown of methylammonium methacrylate, the pressure can no longer be maintained from a bottom temperature of 40° C. From a bottom temperature of 90° C., mist forms in the receiver and the apparatus. This is a clear sign of the reaction of an amine with acid. Immediately after a distillate has been obtained, a solid forms in the bottom and the mixture polymerizes completely within 10 min.

| Time | Bath ° C. | Bottom ° C. | Top ° C. | Pressure mbar | Comment |
|---|---|---|---|---|---|
| 10:24 | 25 | 25 | 25 | 1.6 | start of heating |
| 10:37 | 81 | 60.5 | 27 | 7.4 |  |
| 10:58 | 117 | 92.2 | 45 | 13.1 |  |
| 10:59 | 121 | 94.7 | 59 | 13.0 | mist in receiver |
| 11:01 | 121 | 97.5 | 80 | 13 | 1st fraction, lumps in the liquid phase |
| 11:03 | 123 | 95.6 | 71 | 4.1 |  |
| 11:10 | 129 | 89.7 | 68 | 2.5 | stopped, bottoms polymeric |

Yield: Fraction 1: 16.2 g

COMPARATIVE EXAMPLE 2: PREPARATION OF N-METHYLMETHACRYLAMIDE FROM AQUEOUS METHYLAMINE

Apparatus:
2 l four-neck round-bottom flask with precision glass sabre stirrer, 500 ml dropping funnel, Pt-100 liquid phase thermometer, reflux condenser, cooling bath Mixture:

| 6.15 mol | methacrylic anhydride = | 961.5 g |
|---|---|---|
| 6.15 mol | methylamine, 40% in $H_2O$ = | 477.4 g |

Theoretical Yield:

609.65 g

Procedure:

Methacrylic anhydride is initially charged and cooled to below 10° C. while stirring. Then the metered addition of methylamine is commenced (exothermic reaction, ice bath cooling and slight mist formation). Dropwise addition and cooling are effected such that the temperature does not rise above 10° C. After dropwise addition has ended (4 h), stirring is continued for another 2 h for further reaction; the cooling is removed.

Workup:

The mixture (1419 g) is concentrated on a rotary evaporator with addition of 1000 ppm of octadecyl 3-(3,5-di-tert-butyl-4-hydroxyphenyl)propionate, 500 ppm of hydroquinone monomethyl ether and 20 ppm of 4-hydroxy-2,2,6,6-tetramethylpiperidinooxyl (rad.).

| Residue in the flask: | 229.7 g |
|---|---|
| Distillate to 35 mbar, bath 80° C. | 340.8 g |
| Distillate to 5 mbar, bath 80° C. | 273.4 g |
| Distillate to 0 mbar, bath 80° C.-95° C. | 531.6 g |

GC analysis: (DB5, 30 m, Ø 0.25 mm, film thickness 0.25 µm, 50° C., 3 min isothermal, 14° C./min→280° C., 8 min isothermal; det: 280° C., inj.: 250° C.)

|  | Mass | Water content [g] | Methacrylic acid [GC area %] 4.73 min | N-Methyl-methacryl amide [GC area %] 5.986 min | HBr [GC area %] 13.174 min | Mass of product isolated [g] |
|---|---|---|---|---|---|---|
| Distillate to 35 mbar | 340.8 | 180 | 92.93 | 6.83 |  | 11.0 |
| Distillate to 5 mbar | 273.4 | 83 | 81.02 | 18.74 | 0.03 | 35.7 |
| Distillate to 1 mbar | 531.6 | 20 | 27.36 | 71.06 | 0.84 | 363.5 |
| TOTAL |  |  |  |  |  | 410.2 |

Without neutralization of the aqueous phase, after simple distillation, it is possible to isolate 410.2 g (67.3% of theory) of the product as a mixture with water and methacrylic acid, leaving around 230 g of solids. The distillates to 5 mbar and to 1 mbar (805 g, with 399 g of product) are fractionally distilled in Comparative Example 3.

COMPARATIVE EXAMPLE 3: DISTILLATION OF N-METHYLMETHACRYLAMIDE FROM AQUEOUS METHACRYLIC ACID

Apparatus: 1 l three-neck round-bottom flask, boiling capillary, 30 cm mirrored column with 6×6 Raschig rings, Liebig condenser, Claisen attachment, Thiele-Anschutz attachment, receiver, oil bath, vacuum pump Mixture:

| | |
|---|---|
| 805 g | distillate from Comparative Example 2 |
| 66.5 mg | hydroquinone monomethyl ether (100 ppm) |
| 665 mg | octadecyl 3-(3,5-di-tert-butyl-4-hydroxyphenyl)propionate (1000 ppm) |
| 33.3 mg | 2,4-dimethyl-6-tert-butylphenol (50 ppm) |

Procedure:

| Time | Bath °C. | Bottom °C. | Top °C. | Pressure mbar | Comment |
|---|---|---|---|---|---|
| 00:00 | 20 | 12.0 | 20 | 0.52 | start of heating |
| 00:10 | 98 | 40.7 | 27 | 0.56 | 1st fraction |
| 00:14 | 97 | 50.3 | 30 | 0.72 | |
| 00:19 | 93 | 60.8 | 32 | 2.0 | solids content in liquid phase |
| 00:25 | 96 | 68.4 | 52 | 1.1 | |
| 00:52 | 96 | 69.1 | 42 | 0.35 | |
| 01:22 | 112 | 72.3 | 37 | 0.20 | 2nd fraction, a lot of solids in liquid phase |
| 01:36 | 113 | 73.4 | 38 | 0.21 | significant bumping in the liquid phase, stopped |

| | |
|---|---|
| 1st fraction | 156.3 g |
| 2nd fraction | 48.5 g (cloudy distillate, "mini-lumps") |

The liquid phase is filtered through a porcelain suction filter. Filtrate→292.5 g→GC A sample of the filtercake is dissolved in MeOH→307 g→polymer.

GC analysis: (Meth. F241, DB5, 30 m, Ø 0.25 mm, film thickness 0.25 µm, 50° C., 3 min isothermal, 14° C./min→280° C., 8 min isothermal; det: 280° C., inj.: 250° C.)

| | Mass | Water content [g] | Methacrylic acid [GC area %] 4.73 min | N-Methyl-methacrylamide [GC area %] 5.986 min | HB1 [GC area %] 13.174 min |
|---|---|---|---|---|---|
| 1st fraction | 156.3 | 103 | 99.887 | 0.083 | |
| 2nd fraction | 48.5 | — | 99.616 | 0.320 | |
| Liquid phase filtrate | 292.5 | — | 64.559 | 35.100 | 0.049 |

While it was possible to very substantially isolate water and methacrylic acid, the product prepared with aqueous methylamine polymerizes, and so only around 25% N-methylmethacrylamide was present after distillation for 90 min.

COMPARATIVE EXAMPLE 4: PREPARATION OF N-METHYLMETHACRYLAMIDE FROM AQUEOUS METHYLAMINE, WORKUP BY EXTRACTION

Apparatus: analogous to Comparative Example 2
Mixture:

| | | |
|---|---|---|
| 2.5 mol | F49 (18770-45, 96.61%; 1000 ppm S49) = | 398.9 g |
| 2.5 mol | N-methylamine, 40% in $H_2O$ = | 194.1 g |
| 2.5 mol | ammonia, 25% = | 170 g |

Theoretical Yield: 247.8 g

Procedure: Preparation of the Crude Product Analogous to Comparative Example 2

The crude product is neutralized with $NH_3$ solution, with partial cooling. There was no phase separation.

The mixture is then extracted with MTBE (by GC only methacrylic acid present). This is followed by extraction 3× with 300 ml each time of methyl methacrylate (MMA) and then again 3× with 200 ml each time of MMA (4% product is still present in the last extract). The combined MMA phases are concentrated on a rotary evaporator under reduced pressure (bath temperature 60° C.), with entrainment of $H_2O$ still present.

Yield: 115.8 g

GC analysis: 20.4% methacrylic acid, 69.28% N-methylmethacrylamide

The water/methacrylic acid and N-methylmethacrylamide systems are very similar to one another. Extraction can enable removal of the product only with great effort and poor yield.

COMPARATIVE EXAMPLE 5: PREPARATION OF N-METHYLMETHACRYLAMIDE BY AQUEOUS METHYLAMINE AND NEUTRALIZATION OF THE RESIDUE WITH KOH

Apparatus: 2 l four-neck round-bottom flask with precision glass sabre stirrer, 500 ml dropping funnel, Pt-100 liquid phase thermometer, reflux condenser, ice bath Mixture:

| | |
|---|---|
| 6.0 mol | methacrylic anhydride = 938.1 g |
| 6.0 mol | methylamine, 40% in $H_2O$ = 465.9 g* |

Theoretical Yield: 594.8 g

Procedure: Methacrylic anhydride is initially charged and cooled to below 10° C. Then the metered addition of methylamine is started (exothermic reaction, cooling with ice/$H_2O$, slight mist formation). Dropwise addition and cooling are effected such that the temperature does not rise above 10° C.

After dropwise addition has ended, the mixture is stirred for a further 2 h for further reaction. The cooling is removed.

After storage overnight (mixture becomes pale yellow), the mixture is transferred to a 4 l flask and neutralized with 5.9 mol of KOH (50% in $H_2O$, addition via dropping funnel, cooling with $H_2O$ bath, addition of 2 drops of phenolphthalein solution)→pH 6.5.

The precipitated solids are then filtered off with suction using a porcelain suction filter, and the filtrate is concentrated on a rotary evaporator under reduced pressure (bath up to 80° C., for pressure see below) with addition of 1000 ppm of octadecyl 3-(3,5-di-tert-butyl-4-hydroxyphenyl)propionate, 500 ppm of hydroquinone monomethyl ether and 20 ppm of 4-hydroxy-2,2,6,6-tetramethylpiperidinooxyl (rad.) (based on theoretical yield of N-methylmethacrylamide).

| | | |
|---|---|---|
| Residue on the suction filter | 77.5 g | (b) |
| Residue in the flask | 1026.2 g | (a) |

GC analysis: (DB5, 30 m, Ø 0.25 mm, film thickness 0.25 µm, 50° C., 3 min isothermal, 14° C./min→280° C., 8 min isothermal; det: 280° C., inj.: 250° C.)

To ascertain the mass of the product in the fraction, an exactly defined amount of dimethylaminopropylmethacrylamide is added and the exact mass is determined via the comparison of the integrals.

On neutralization of the aqueous phase with KOH, after distillation, it is possible to isolate only 144.9 g (29.6% of theory) of the product as a dilute aqueous solution.

COMPARATIVE EXAMPLE 6: PREPARATION OF N-METHYLMETHACRYLAMIDE BY AQUEOUS METHYLAMINE AND NEUTRALIZATION OF THE RESIDUE WITH NAOH

Apparatus: 2 l four-neck round-bottom flask with precision glass sabre stirrer, 500 ml dropping funnel, Pt-100 liquid phase thermometer, reflux condenser, cooling bath Mixture:

6.0 mol methacrylic anhydride=938.1 g 6.0 mol methylamine, 40% in $H_2O$=465.9 g*

Theoretical Yield: 594.8 g

Procedure: Methacrylic anhydride is initially charged and cooled to below 10° C. Then the metered addition of methylamine is started (exothermic reaction, cooling with ice/$H_2O$, slight mist formation). Dropwise addition and cooling are effected such that the temperature does not rise above 10° C. After dropwise addition has ended, stirring is continued for another 2 h for further reaction; the cooling is removed.

Subsequently, the mixture is transferred to a 4 l flask and neutralized with 5.9 mol of 50% NaOH in $H_2O$ (236 g of NaOH, 236 g of $H_2O$*) by addition via dropping funnel while cooling with an $H_2O$ bath and addition of 2 drops of phenolphthalein solution up to pH 6.5-pH 7.0.

The precipitated solids are filtered off using a porcelain suction filter→very poor filtration since the solid is waxy.

Filtrate: 1634 g

For analysis, in a GC vial, 1.5 g of filtrate are admixed with an internal standard and this is used to determine the content of N-methylmethacrylamide:

Calculated product content by GC analysis: 36.4%~99.9% of theory.

The filtrate is concentrated on a rotary evaporator under reduced pressure (1). The condensate condensed (frozen) on the condenser is thawed out overnight and, the next day, the residue flask is concentrated once again to dryness at bath temperature 80° C. and 1 mbar (2). In the course of this, significant amounts of solids precipitate out. The distillates obtained are analysed by means of GC.

| | Mass [g] | LB 1.09–1.20 min | Methacrylic acid [GC area %] 4.73 min | N-Methyl-methacryl amide [GC area %] 5.986 min | HB1 [GC area %] 13.174 min | Proportion of product in fraction [% by wt.] | Mass of product isolated [g] |
|---|---|---|---|---|---|---|---|
| Dist. to 60 mbar | 316.4 | 1.081 | 6.121 | 89.158 | 1.113 | 7.0 | 22.15 |
| Dist. to 1 mbar | 163.8 | 1.110 | 8.088 | 90.161 | 0.090 | 94.5 | 154.05 |

LB = low boilers

GC: (DB5, 30 m, Ø 0.25 mm, film thickness 0.25 μm, 50° C., 3 min isothermal, 14° C./min→280° C., 8 min isothermal; det: 280° C., inj.: 250° C.)

| Sample | Mass [g] | Product content by GC (as described in CE5) [% by wt.] | Product mass [g] |
|---|---|---|---|
| Filtrate | 1634 | 36.4 | 594.8 |
| Distillate to 60 mbar | 172.2 | 14.0 | 24.1 |
| Distillate flask | 7.5 | 79.3 | 6.0 |
| thawed out from the condenser (1) | 230.6 | 23.1 | 53.3 |
| thawed out from the condenser (2) | 129.2 | 47.7 | 61.6 |
| Total distillates | 539.5 | | 144.9 |

On neutralization of the aqueous phase with NaOH, after distillation, it is possible to isolate only 144.9 g (24.4% of theory) of the product as a dilute aqueous solution.

The invention claimed is:

1. A process for preparing N-methyl(meth)acrylamide, comprising reacting (meth)acrylic anhydride with methylamine, wherein:
   a) the methylamine has a water content of <1% by weight;
   b) the molar ratio of (meth)acrylic anhydride:amine is 1:x wherein 1≤x<2;
   and wherein the reaction has a yield of greater than 90%.

2. The process of claim 1, wherein the reaction is performed in the presence of a stabilizer.

3. The process of claim 2, wherein the stabilizer is selected from the group consisting of: phenothiazine, 2,4-dimethyl-6-tert-butylphenol, N,N'-diphenyl-p-phenylenediamine, 4-hydroxy-2,2,6,6-tetramethylpiperidinooxyl, 4-methyl-2,6-di-tert-butylphenol, 2-tert-butyl-6-(3-tert-butyl-2-hydroxy-5-methylbenzyl)-4-methylphenyl acrylate, benzene-1,4-diamine, N,N'-mixed phenyl and tolyl derivatives (DTPD), 2,6-di-tert-butyl-alpha-(dimethylamino)-p-cresol, tert-butylcatechol, bis-2,2,6,6-tetramethyl-4-piperidyl sebacate, 2,2,6,6-tetramethylpiperidine N-oxyl and mixtures thereof.

4. The process of claim 1, wherein the water content of the methylamine is less than 0.1% by weight.

5. The process of claim 1, wherein the water content of the reaction mixture after the end of addition of all reactants is less than 10% by weight.

6. The process of claim 5, wherein the water content of the reaction mixture after the end of addition of all reactants is less than 5% by weight.

7. The process of claim 5, wherein the water content of the reaction mixture after the end of addition of all reactants is less than 1% by weight.

8. The process of claim 5, wherein the water content of the reaction mixture after the end of addition of all reactants is less than 0.1% by weight.

9. The process of claim 1, wherein the reaction is conducted in a polar aprotic solvent.

10. The process of claim 1, wherein the methylamine is added in liquid or gaseous form.

11. The process of claim 1, wherein the methylamine is added as a gas.

12. The process of claim 1, wherein the molar ratio of (meth)acrylic anhydride:amine is from 1:1 to 1:1.5.

13. The process of claim 1, wherein the (meth)acrylic acid by-product is removed or separated by distillation.

14. The process of claim 1, wherein the (meth)acrylic anhydride is reacted with methylamine at temperatures between −20° C. and 100° C.

15. The process of claim 1, wherein the (meth)acrylic anhydride is reacted with methylamine at a temperature between 0° C. and 80° C.

16. The process of claim 1, wherein the (meth)acrylic anhydride is reacted with methylamine at a temperature between 20° C. and 50° C.

17. The process of claim 1, wherein the (meth)acrylic anhydride is reacted with methylamine at an absolute pressure of 0.5 bar to 10 bar.

18. The process of claim 1, wherein the (meth)acrylic anhydride is reacted with methylamine at an absolute pressure of 1 bar to 5 bar.

19. The process of claim 3, wherein the (meth)acrylic anhydride is reacted with methylamine at an absolute pressure of 0.5 bar to 10 bar.

20. The process of claim 19, wherein the molar ratio of (meth)acrylic anhydride:amine is 1:1.

* * * * *